United States Patent
Choi

(10) Patent No.: US 6,371,451 B1
(45) Date of Patent: Apr. 16, 2002

(54) SCENT DIFFUSION APPARATUS AND METHOD

(75) Inventor: Joong Ho Choi, Gyunggi-do (KR)

(73) Assignee: Korea Institute of Science and Technology (KR)

( * ) Notice: Subject to any disclaimer, the term of this patent is extended or adjusted under 35 U.S.C. 154(b) by 0 days.

(21) Appl. No.: 09/534,882

(22) Filed: Mar. 24, 2000

(30) Foreign Application Priority Data

Oct. 29, 1999 (KR) .............................................. 99-47612
Oct. 29, 1999 (KR) .............................................. 99-47613

(51) Int. Cl.$^7$ ................................ B01F 3/04; G06F 9/00
(52) U.S. Cl. .................. 261/26; 261/115; 261/DIG. 88; 261/DIG. 89
(58) Field of Search ............................ 261/115, 26, 141, 261/142, DIG. 17, DIG. 65, DIG. 88, DIG. 89; 96/222; 422/124

(56) References Cited

U.S. PATENT DOCUMENTS

| | | | | |
|---|---|---|---|---|
| 4,396,557 A | * | 8/1983 | DeLuca ................ | 261/DIG. 17 |
| 4,603,030 A | * | 7/1986 | McCarthy ............ | 261/DIG. 17 |
| 4,629,604 A | * | 12/1986 | Spector ................ | 261/DIG. 88 |
| 5,023,020 A | * | 6/1991 | Machida et al. ...... | 261/30 |
| 5,167,877 A | * | 12/1992 | Pai ........................ | 261/30 |
| 5,297,988 A | * | 3/1994 | Nishino et al. ...... | 454/75 |
| 5,565,148 A | * | 10/1996 | Pendergass, Jr. ..... | 261/DIG. 88 |
| 5,591,409 A | * | 1/1997 | Watkins ................ | 422/110 |
| 5,724,256 A | * | 3/1998 | Lee et al. .............. | 422/110 |
| 6,004,516 A | * | 12/1999 | Rasouli et al. ....... | 422/124 |
| 6,024,783 A | * | 2/2000 | Budman ................ | 96/222 |

* cited by examiner

Primary Examiner—David A. Simmons
Assistant Examiner—Frank M. Lawrence
(74) Attorney, Agent, or Firm—Bourque & Associates, P.A.

(57) ABSTRACT

A scent diffusion apparatus and method contains individual original scents for a plurality of scents to be diffused, constructs information on position information of the contained original scents and information on various scents to be diffused in a database, and mixes the original scents of the desired scent properly at a desired point in time based on the scent information, to thereby spray the desired scent. The scent diffusion method includes providing a plurality of scent spraying units containing original scents, heating the original scents via a heater, evaporating the original scents, and diffusing the evaporated scent with the air via an air supply pump. Thus, a desired scent can be transferred to a selected subject under correct concentration. The scent diffusion apparatus uses scent cartridges containing the original scents, such as cartridges used in an existing ink-jet printer, and uses the same control commands as those of a general personal computer or ink-jet printer compatibly. Thus, the scent diffusion apparatus can control an amount of diffusion precisely, be manufactured in a compact fashion, and used in connection with a general purpose computer in which almost all kinds of operating systems supporting an ink-jet printer are incorporated.

34 Claims, 9 Drawing Sheets

SCENT DIFFUSION APPARATUS AND METHOD

FIELD OF THE INVENTION

The present invention relates to a scent diffusion apparatus and method, and more particularly, to an apparatus and method in which original scents for scents to be diffused are individually contained and original scents for the desired scent are properly mixed at a desired point in time based on scent information on various scents stored in a database in advance, to thereby diffuse the desired scent.

BACKGROUND AND PRIOR ART

U.S. Pat. No. 5,487,502 is disclosed as technology related to the present invention. This patent is technology for diffusing a scent and outputting a sound for a decorative article, which includes a container containing compressed liquid for making a scent therein, a driver for opening and closing a valve for the container, a diffusion tube connected to the container, a plurality of nozzles and a sound generator. A controller controls the decorative article to open the valve of the container to diffuse the scent and output the sound, in order to enhance a decorative effect.

As another related prior art, U.S. Pat. No. 5,277,341 is disclosed. This patent discloses a spraying apparatus for spraying liquid by means of a pump which is repeatedly driven by a solenoid, which includes the pump, a piston, a pusher and an actuator.

As still another related prior art, U.S. Pat. No. 5,417,258 is disclosed. This patent discloses a rechargeable liquid spraying apparatus which includes an actuator head, a tank containing liquid, an angular position mechanism and an axial position mechanism, in which a pump is installed in the tank.

As yet another related prior art, U.S. Pat. No. 5,221,025 is disclosed. This patent discloses a method and apparatus for spraying a medicine, scent or liquid in the form of liquid or gas.

However, in the above related prior art, liquid is sprayed into the air as liquid particles using a nozzle, and a vaporization rate is changed according to time based on change of temperature or peripheral circumstance. Thus, a desired scent could not be emitted to a desired subject at a correct concentration. Therefore, it becomes a much bigger problem when a few scents are desired to be mixed at a correct concentration to produce a new scent.

It is also difficult to manufacture a diffusion unit in a compact fashion, since the above related prior art uses a device for containing the compressed liquid or a device for compressing liquid. It is also difficult to control an amount of diffusion precisely. The prior art using a separate controller cannot be interfaced with a general purpose computer. In particular, technologies for mixing and controlling scents should be developed separately.

SUMMARY OF THE INVENTION

To solve the above problems, it is an object of the present invention to provide a scent diffusion apparatus for evaporating a scent and diffusing the evaporated scent in the air.

It is another object of the present invention to provide a scent diffusion apparatus which can be manufactured in a compact fashion and can be interfaced with a general purpose computer, in which an amount of diffusion can be controlled precisely.

It is still another object of the present invention to provide a scent diffusion apparatus and method for mixing original scents for a desired scent precisely at a desired point in time and diffusing the desired scent.

To accomplish the above object of the present invention, there is provided a scent diffusion apparatus comprising: scent spraying means containing individual original scents, for diffusing and spraying a desired scent using at least one original scent among the contained original scents; a first storing unit for storing position information of each of the individual original scents contained in the scent spraying unit; a second storing unit for storing information on the scents to be diffused; a timer for setting a point in time of diffusion of a scent to be diffused; and a controller for reading position information on the original scents and information on the scents to be diffused from the first and second store units, setting a scent diffusion point in time in the timer according to the information read, and controlling a scent to be diffused in the scent spraying unit at the set point in time.

The scent spraying means comprises a plurality of scent spraying units, wherein each spraying unit comprises: a container containing the original scent; an opening and closing unit for receiving the sealed container; a heater for evaporating the scent in the container; an air intake unit for allowing air to enter the scent diffusion apparatus; and an outlet unit for discharging a scent mixture in which the intake air is mixed with the scent evaporated by the heater.

The first storing unit constructs positions of the scent spraying units with respect to the original scents in the database, and stores the same in the database.

The second storing unit constructs in a database the kind, constituent ratio, concentration and diffusion condition of individual original scents necessary for diffusing a desired scent with respect to scents to be diffused, and stores the same in a database.

Also, the scent spraying means comprises a single scent spraying unit, wherein each scent spraying unit comprises: a plurality of scent cartridges storing the original scents individually; spraying nozzles provided in each of the plurality of the scent cartridges, for spraying the original scents contained in the scent cartridges; an evaporation dish for evaporating the original scents sprayed from the scent cartridges via the spraying nozzles; an air intake unit for providing a source of external air; and an air outlet unit for discharging a mixed gas in which the intake air is mixed to form the scent evaporated by the evaporation dish.

There is also provided a scent diffusion method according to the present invention, comprising the steps of: (a) storing a plurality of individual original scents; (b) constructing and storing, in a database, information necessary for producing a scent to be diffused; (c) reading information concerning a scent to be diffused from the database constructed in step (b); and (d) mixing and spraying the corresponding one or more individual original scents according to the information read in step (c).

BRIEF DESCRIPTION OF THE DRAWINGS

The above objects and other advantages of the present invention will become more apparent by describing the preferred embodiments thereof in more detail with reference to the accompanying drawings in which.

DETAILED DESCRIPTION OF THE PREFERRED EMBODIMENT

Figure 1:
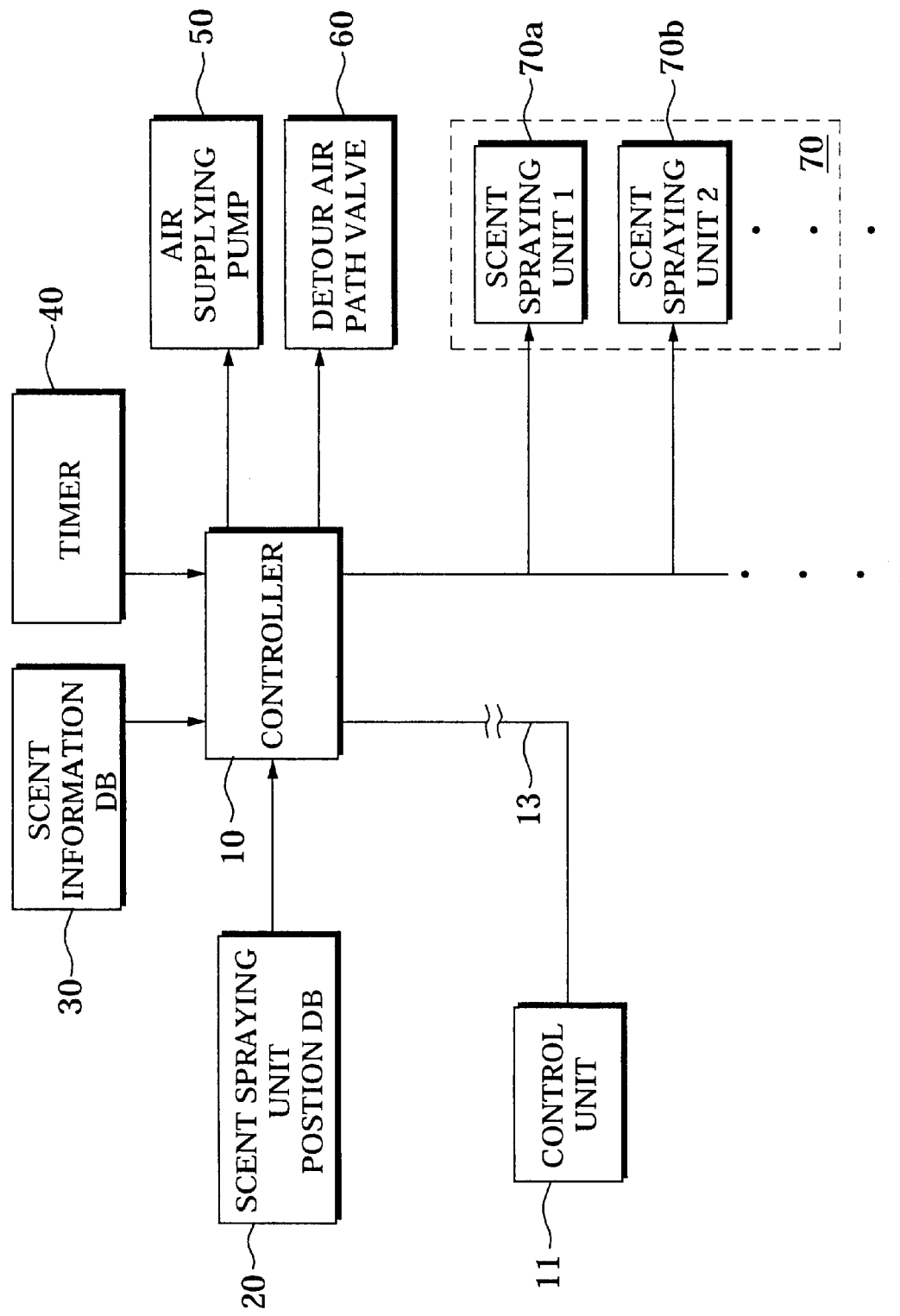
FIG. 1 is a block diagram showing a scent diffusion apparatus according to a preferred embodiment of the present invention.

Referring to FIG. 1, a scent diffusion apparatus includes a plurality of scent spraying units 70 for spraying scents, an air supplying pump 50 for supplying air to the plurality of scent spraying units 70 and a timer 40 for controlling a point in time to diffuse a scent at each of the scent spraying units 70. A scent information database 30 stores information on scents provided to the plurality of scent spraying units 70. The apparatus also includes a scent spraying unit position database 20 storing position information of each of the scent spraying units 70, a detour air path valve 60, and a controller 10, for reading the position and scent content of the scent spraying unit 70 to be controlled from the scent spraying unit position database 20, and for reading information on a scent to be diffused from the scent information database 30, to thereby control one or more of the scent spraying units 70 to diffuse the scent. The structure of each of the scent spraying units 70 will be described in more detail with reference to FIG. 2.

Figure 2:
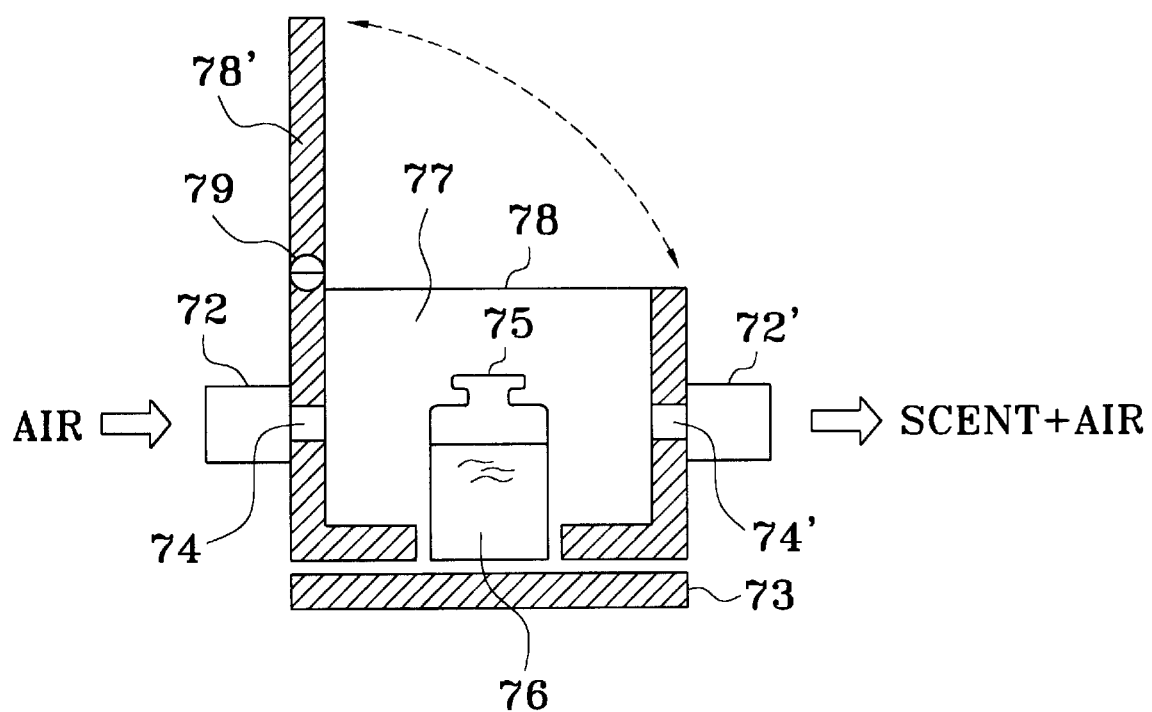
FIG. 2 shows the scent spraying unit 70 of FIG. 1 in greater detail.

FIG. 2 shows the scent spraying unit 70 of FIG. 1 in detail. The scent spraying unit 70 shown in FIG. 2 includes an original scent 76 which is used for mixing with air at a predetermined ratio in order to make a scent to be desired, an intake solenoid valve 72 for providing a source of air supplied from the air supplying pump 50 under the control of the controller 10, and an outlet solenoid valve 72' for discharging a mixture containing air and scent. The original scent 76 is preferably contained in a container 75 in the form of liquid. The scent spraying unit 70 of FIG. 2 includes a heater 73 for evaporating a scent in the container 75 under the control of the controller 10, an opening and closing portion 78 for containing and sealing the scent evaporated from the container 75, and a space portion 77 for maintaining the evaporated original scent gas at a constant volume. The plurality of scent spraying units 70 each having the above structure are aligned in a one-dimensional, two-dimensional or three-dimensional array.

It is preferable to mix the original scent 76 with air at a desired ratio for the purpose of creating a predetermined volume ratio of gaseous phase of each component. In order to mix the gaseous phase of each component using a volume ratio, an opening and closing time of the solenoid valve 72' and a sectional area of an outlet 74' are controlled, so that a concentration of the constituent of the original scent 76 is adjusted.

It is preferable that the controller 10 reads information on the constituent ratio of each original scent 76 forming a scent to be finally diffused from the scent information database 30 and simultaneously controls each scent spraying unit 70 based on the previously read constituent ratio information, to thereby diffuse a desired scent repeatedly. It is also preferable that the controller 10 controls each of the scent spraying units 70 to diffuse a respectively different scent or the plurality of the scent spraying units 70 to diffuse the same scent.

It is preferable that the controller 10 is controlled by a control unit 11, such as a computer, from a remote place using a predetermined protocol by wire or wireless connection 13, to thereby diffuse a predetermined scent. It is preferable that the original scent 76 includes one or more scent components. It is preferable that a rubber band type heater is used as the heater 73. It is preferable that driving of the air supplying pump 50, temperature of the heater 73 and the intake and outlet solenoid valves 72 and 72' are controlled together when the plurality of scent spraying units 70 are controlled.

Figure 3:
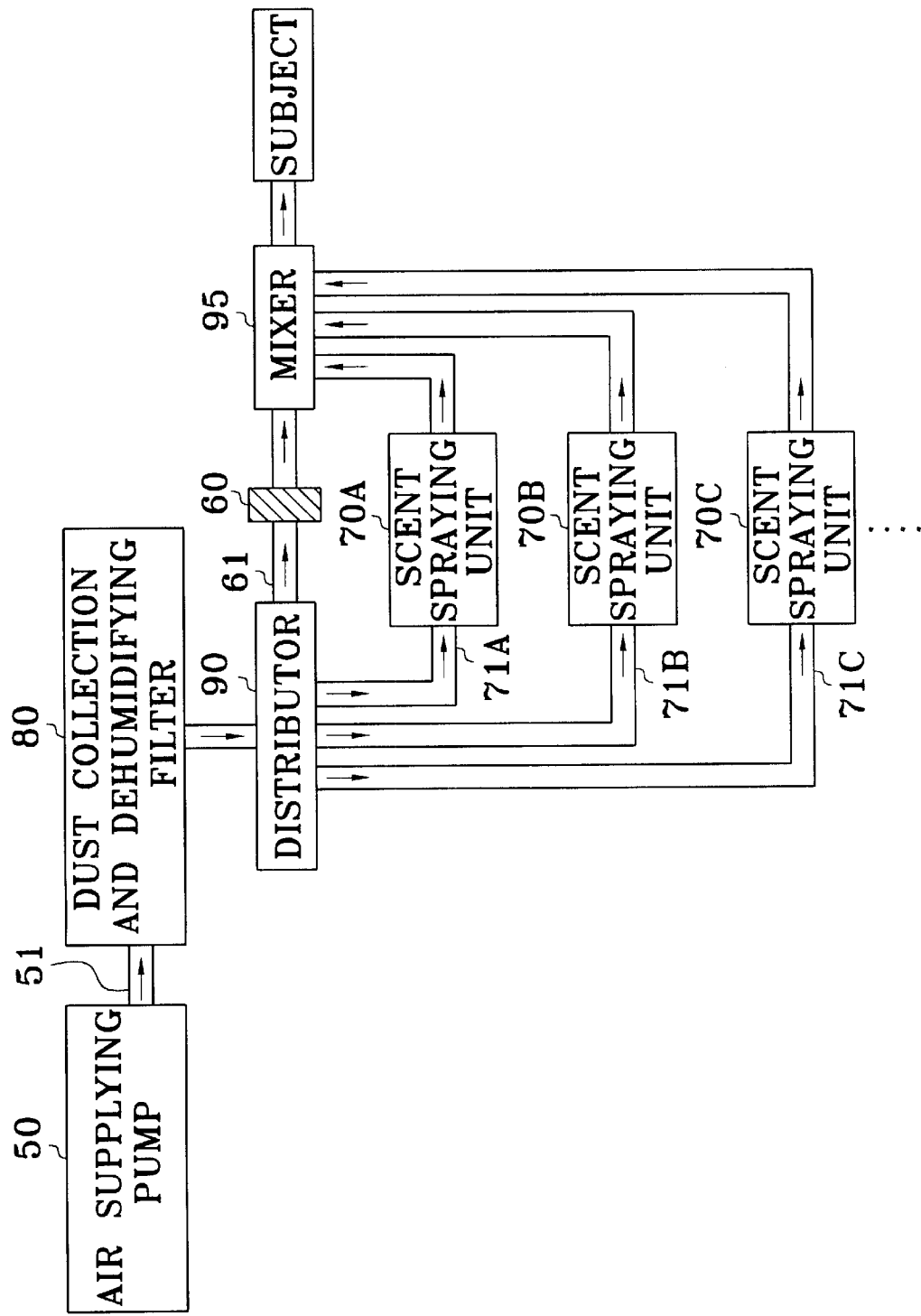
FIG. 3 is a piping diagram showing a flow of an air-mixture gas of the apparatus of FIG. 1.

FIG. 3 is a piping diagram showing a flow of an air-mixture gas of the FIG. 1 apparatus. Dust is removed from the air supplied from the air supplying pump 50. For this purpose, the present invention includes a dust collection and dehumidifying filter 80, for removing dust and humidity from the intake air, as well as a distributor 90, for distributing the air having passed through the dust collection and dehumidifying filter 80 to the plurality of scent spraying units 70. A mixer 95 mixes the scent diffused from the plurality of scent spraying units 70 with air, to thereby produce a uniform air-scent mixture. A detour air path valve 60 is installed between the distributor 90 and the mixture 95. The scent-air mixed in the mixer 95 is transferred to a desired subject via a scent provider (not shown). A tube or a delivery method to the subject (including a subject intaker) can be used as the scent provider. Compressed air is used as a scent carrier.

Referring to FIG. 3, air flow and one or more scents are mixed into the air at an appropriate ratio, to then be transferred to a selected subject. In more detail, the compressed air supplied from the air supplying pump 50 is supplied to the dust collection and dehumidifying filter 80 and the distributor 90 via an air supplying path 51, and then flows into each of the plurality of scent spraying units 70 via the intake solenoid valves 72 after having passed through respective air supplying paths 71. The air mixed with the scent in each of the scent spraying units 70 is discharged via the outlet solenoid valve 72' and then into the mixer 95.

At the distributor 90, part of air passes through an air supplying path 61 and is supplied to the mixer 95 via a detour air path valve 60. Accordingly, at the mixer 95, the concentration of the mixture gas of the air and the scent flown from each scent spraying unit 70 can be adjusted. That is, the detour air path valve 60 supplies air when gases discharged from each of the plurality of scent spraying units 70 are mixed to produce a scent mixture gas to be desired, to thereby adjust the concentration of a finally produced scent. Only air which is not mixed with any scent flows through the detour air path valve 60 after or before diffusing a particular scent, to thereby refresh a residual scent in the apparatus.

The operation of the scent diffusion apparatus according to the present invention having the above structure will be described in more detail.

Figure 4:
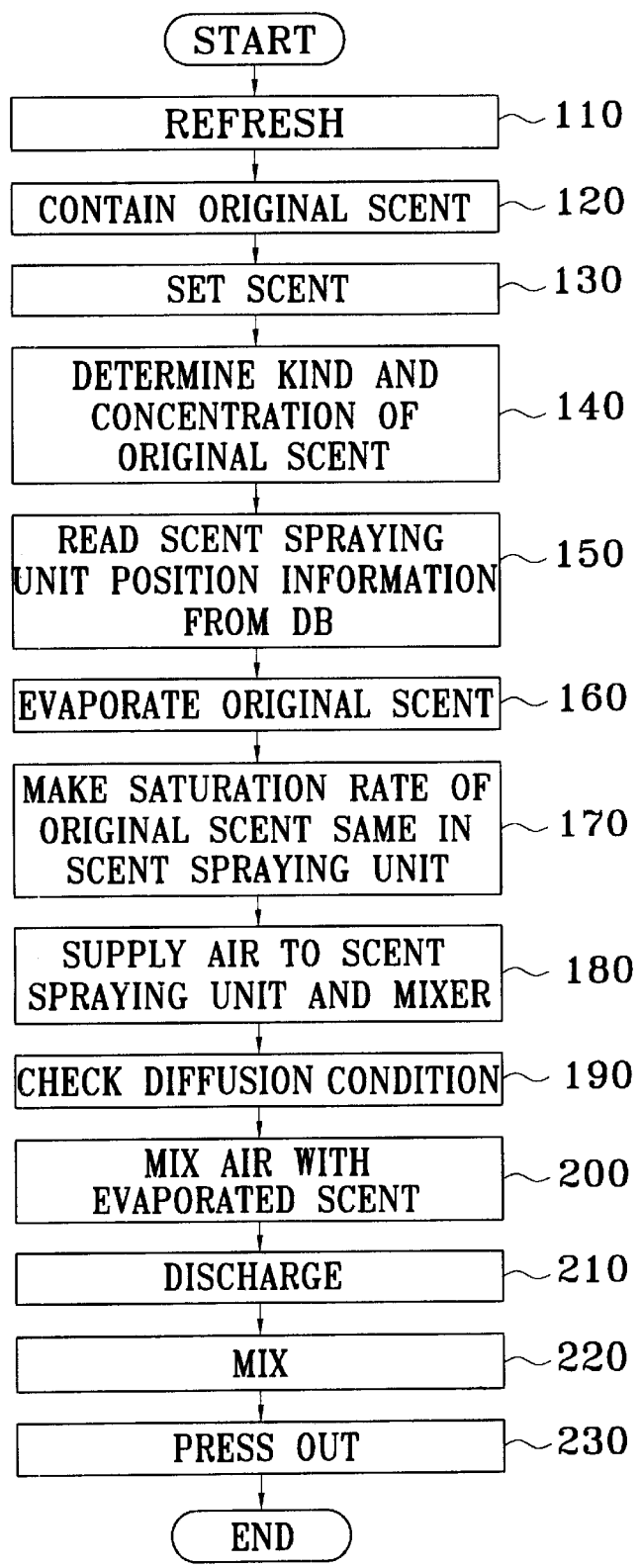
FIG. 4 is a flowchart view for explaining the scent diffusion method of the apparatus of FIG. 1.

FIG. 4 is a flow chart explaining the scent diffusion method of the apparatus of FIG. 1. In FIG. 4, only air which is not mixed with any scent flows through the detour air path valve 60 before diffusing a scent, to thereby refresh or purge a residual scent in the apparatus (step 110). Then, one or more original scents 76 to be used for diffusing a scent is contained (step 120), and a scent to be diffused is established (step 130). In step 130, to produce the established scent, the controller 10 reads information on which of the individual original scent(s) are 76 to be combined, the concentration thereof and an diffusion condition from the scent information database 30 (step 140).

The diffusion condition includes a point in time to be diffused, a diffusion duration time, and a diffusion strength. The controller 10 also reads position information of each scent spraying unit 70 containing the original scent 76, from the scent spraying unit position database 20 (step 150). To diffuse the established scent, the controller 10 drives a heater 73 in one or more corresponding scent spraying unit(s) 70 based on the information read from the databases 20 and 30, and vaporizes the original scents 76 a predetermined amount (step 160). The controller 10 controls driving of the heater 73 so that the saturation rates of the original scents 76 vaporized by the heating of the heater 73 in the respective spraying units 76 are the same (step 170). In step 170, a vaporization rate according to the temperature of the original scent 76 is differently set depending upon the position where the original scent 76 has been contained.

The controller 10 then actuates the air supplying pump 50 in order to supply air to each of the scent spraying unit 70 and the mixer 95 (step 180). The air supplied from the air supplying pump 50 actuated by step 180 is filtered through the dust collection and dehumidifying filter 80, to thereby remove dust and humidity. The distributor 90 distributes the filtered air to each of the scent spraying units 70 and the detour air path valve 60 via the air supplying paths 71 and 61. The controller 10 checks a diffusion condition (step 190).

If a current time is a diffusion point in time, the solenoid valves 72 and 72' in the scent spraying unit 70 containing the original scent 76 constituting a scent to be diffused are controlled to mix air with the evaporated scent (step 200). The opening and closing period of the intake and outlet solenoid valves 72 and 72' is controlled in proportion with a time in order to adjust a concentration of the mixture of the air and the evaporated scent in each scent spraying unit 70. The controller 10 controls the scent mixed with the air in each scent spraying unit 70 to be discharged to the mixer 95 via the outlet 74' (step 210). The mixer 95 uniformly mixes the heated and evaporated scent gases which are mixed with the air and discharged from each scent spraying unit 70 (step 220). The uniformly mixed gases are exhausted due to a pressure difference, to a selected subject (step 230).

Figure 5:
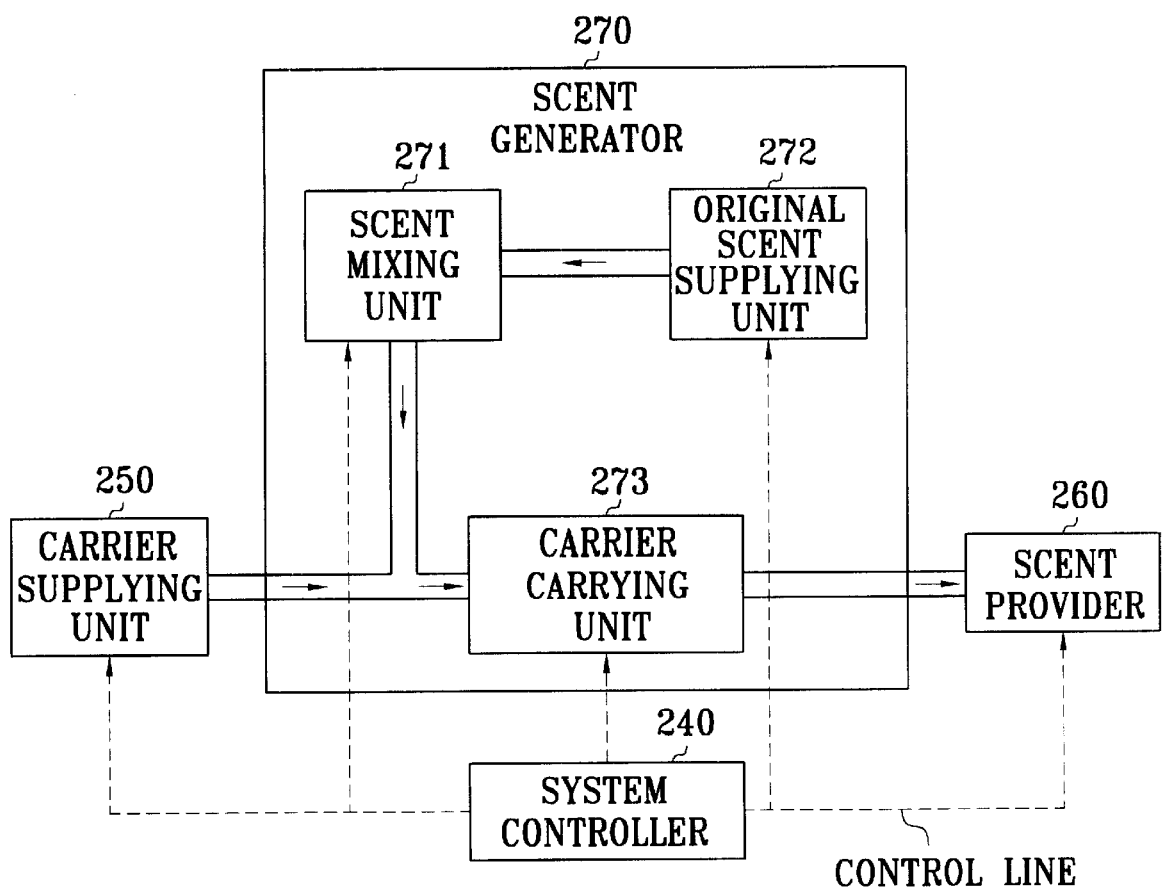
FIG. 5 is a block diagram showing a scent diffusion apparatus according to another embodiment of the present invention.

FIG. 5 is a block diagram showing a scent diffusion apparatus according to another embodiment of the present invention. The apparatus shown in FIG. 5 includes a carrier supplying unit 250 for supplying a scent carrier, a scent generator 270 for generating a scent, and a scent provider 260 for diffusing the scent generated by the scent generator 270 to a selected subject. The FIG. 5 apparatus also includes a system controller 240 for controlling the carrier supplying unit 250, the scent generator 270 and the scent provider 260. Here, the scent generator 270 includes a unit 272 for supplying an original scent, a unit 271 for mixing the supplied original scent with air and a carrier carrying unit 273 for carrying the mixed scent to the scent provider 260.

An innoxious and inodorous inactive gas including air or innoxious and inodorous liquid including water is used as the carrier. The carrier carrying unit 273 uses a pipe or an air flow. The scent provider 260 includes a device such as a nozzle so that a carrier reaches a selected subject, which means a scent inhalation unit operating in front of the nose of a selected subject.

It is preferable that a device for generating a pressure such as an air blower fan, a compressor and a pump is used as the scent carrier supplying unit 250. It is preferable that the original scent supplying unit 272 is an automatic scent supplying device. The original scent mixing unit 271 is a device for adjusting a mixing ratio of the scent by means of various valves and heaters.

The unit 273 for carrying the carrier mixed with the scent is a device for mixing the scent carrier with the scent while passing through the scent generator 270, and directly supplying the mixed carrier to the subject using a flow of fluid or a flow control, or supplying it via a carrier induction tube and the scent provider 260.

Figure 6:
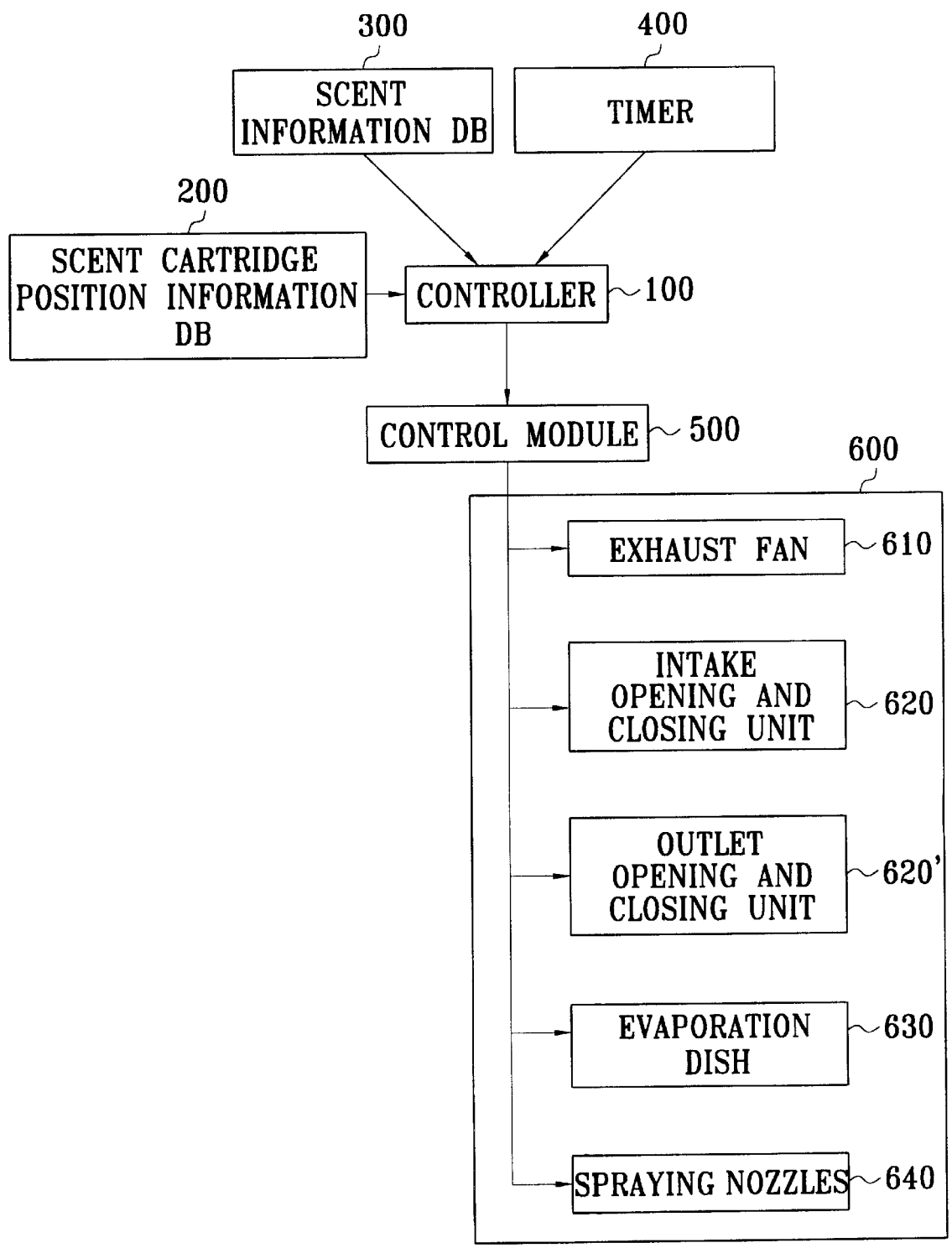
FIG. 6 is a block diagram showing a scent diffusion apparatus according to another embodiment of the present invention.

FIG. 6 is a block diagram showing a scent diffusion apparatus according to another preferred embodiment of the present invention. The scent diffusion apparatus of FIG. 6 includes a scent spraying unit 600 for individually containing original scents for various scents to be diffused and mixing and spraying the contained original scents properly. The scent spraying unit 600 according to the present invention is constructed to use scent cartridges containing original scents, similar to ink cartridges used in a conventional ink-jet printer. A scent cartridge position information database 200 stores position information of each of the scent cartridges in the scent spraying unit 600 with respect to the original scents stored in the scent spraying unit 600. A scent information database 300 stores information on various scents to be diffused. A timer 400 is used for setting a point in time for diffusing a scent. A controller 100 reads information for a scent to be diffused from the scent cartridge position information database 200 and the scent information database 300, and sets a desired time in the timer 400. Also, the controller 100 controls a control module 500 to supply control signals to the scent spraying unit 600 so that the scent spraying unit 600 sprays a desired scent.

Figure 7:
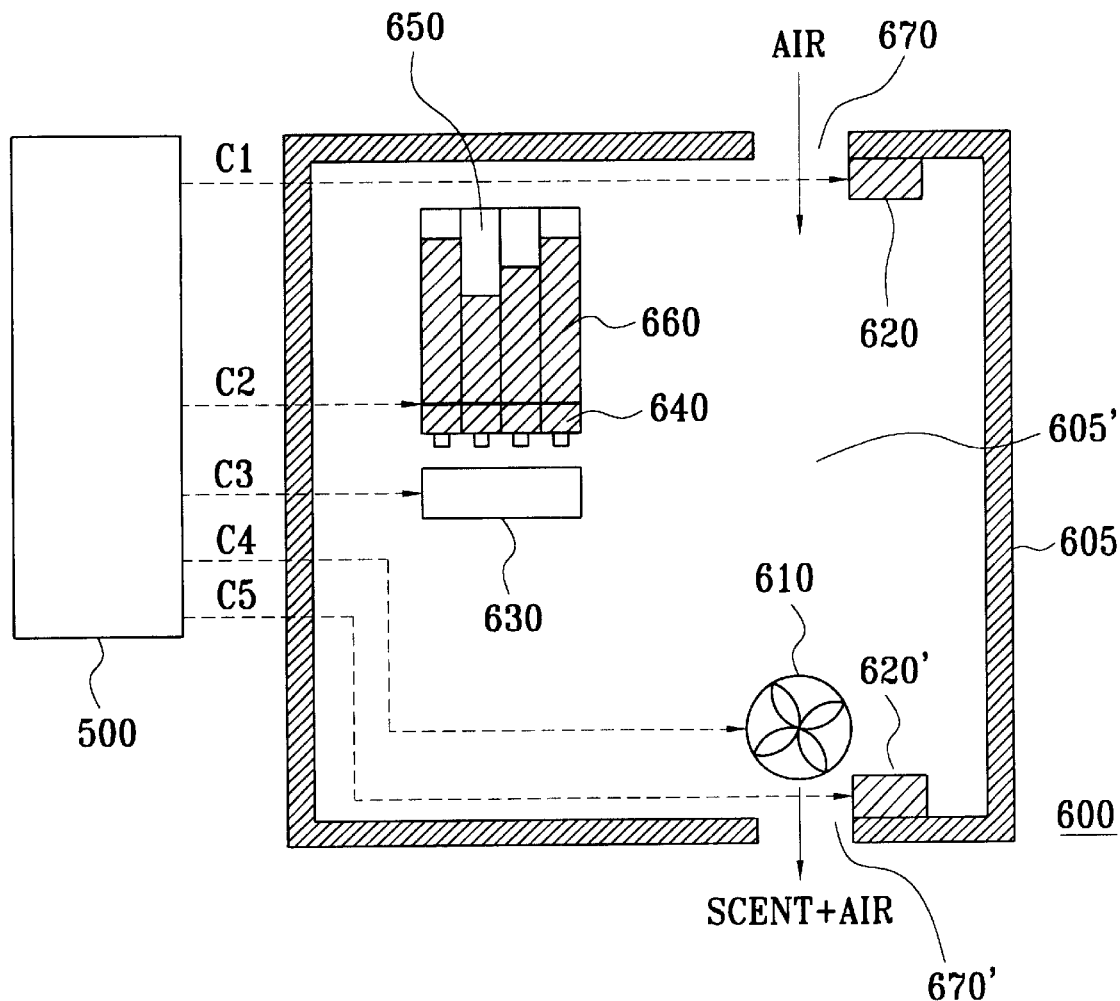
FIG. 7 shows a scent spraying unit 600 of FIG. 6 in greater detail.

FIG. 7 shows the scent spraying unit 600 of FIG. 6 in detail. The scent spraying unit 600 includes a plurality of scent cartridges 650 containing original scents, spraying nozzles 640 provided in one end of each of the scent cartridges 650, and an evaporation dish 630 installed in a position where original scents sprayed from the spraying nozzles 640 are received and contained, for evaporating the sprayed original scents. The plurality of scent cartridges 650 and the evaporation dish 630 are provided in a sealed container 605. An intake hole 670 for providing a source of air is provided in one side of the sealing container 605, and an outlet hole 670' for discharging a mixture of the intake air and the evaporated scent is provided in the other side of the sealed container 605. The scent spraying unit 600 also includes an electrically-driven intake opening and closing unit 620 for controlling an amount of intake air brought in via the intake hole 670, an electrically-driven outlet opening and closing unit 620' for controlling an amount of the mixed gas discharged via the outlet hole 670', and an exhaust fan 610 for discharging the mixture gas out of the sealed container 605.

In the scent spraying unit 600 of FIG. 7, the spraying nozzles 640 may include a piezoelectric or thermal jet spray type nozzle.

Figure 8:
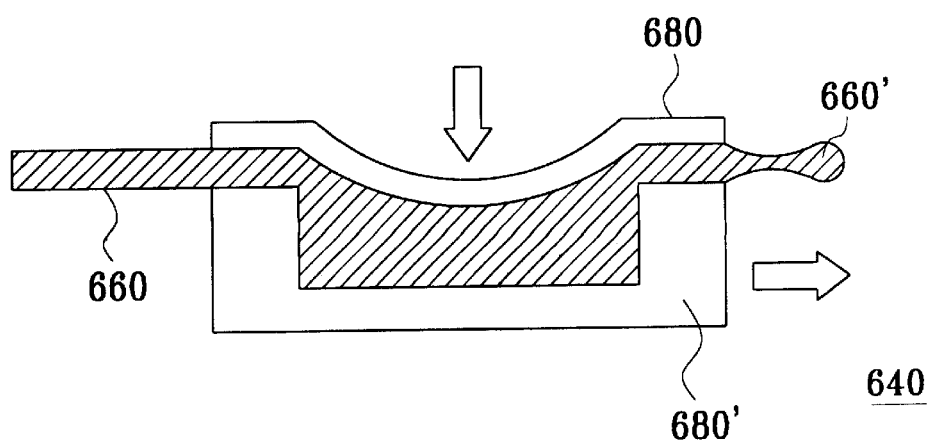
FIG. 8 is a diagram showing a spraying nozzle 640 of FIG. 7 which is employed in one embodiment of the present invention.

FIG. 8 is a diagram showing a spraying nozzle 640 of FIG. 7 which is embodied using a piezoelectric method. In FIGS. 7 and 8, a hatched portion indicates a original scent 660 contained in a scent cartridge. It is preferable that the original scent 660 is in the form of liquid. When piezoelectric plates 680 and 680' are depressed according to a control signal C2 supplied from the control module 500, a liquid scent positioned between the piezoelectric plates 680 and 680' is pushed out according to the generated pressure. The pushed-out liquid scent 660' is separated from the liquid scent 660 in the scent cartridge and is contained in the evaporation dish 630 of FIG. 2. It is preferable that the spraying nozzle of the piezoelectric plate method is controlled to be closed with a cover (not shown) in those times other than a spraying operation. It is also preferable that a residual liquid scent is inhaled whenever each spraying operation is terminated in order to prevent the spraying nozzles from being clogged.

Figure 9:
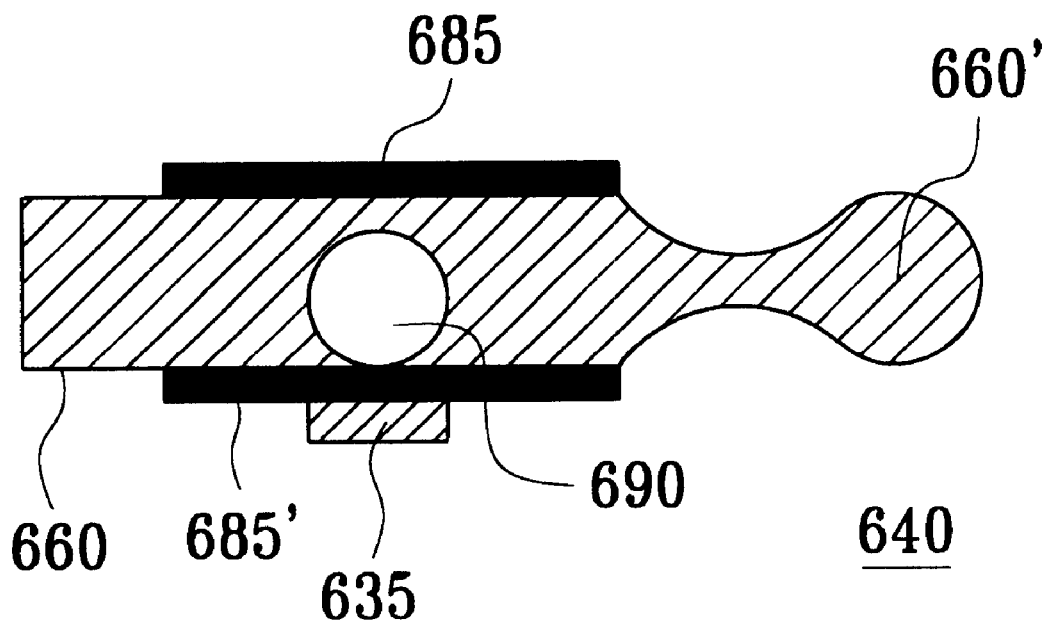
FIG. 9 is a diagram showing a spraying nozzle 640 of FIG. 7 which is employed in a thermal jet method in accordance with another embodiment of the present invention.

FIG. 9 is a diagram showing a spraying nozzle 640 which is utilized in a thermal jet method. In the spraying nozzle of FIG. 9, a heater 635 applies heat to nozzles 685 and 685' according to a control signal C2 supplied from the control module 500. Here, it is preferable that the heater 635 heats the nozzles 685 and 685' within a time as short as possible. If the nozzles 685 and 685' have been heated, the volume of an air bubble 690 contained therein is expanded. The expanded air bubble 690 pushes out the liquid scent 660 out of the nozzles 685 and 685'. The amount of the pushed-out liquid scent 660' corresponds to the expanded volume of the air bubble 690. The liquid scent 660' pushed out of the nozzles 685 and 685' is separated from the liquid scent 660 and is contained on the evaporation dish 630 of FIG. 7.

Figure 10:
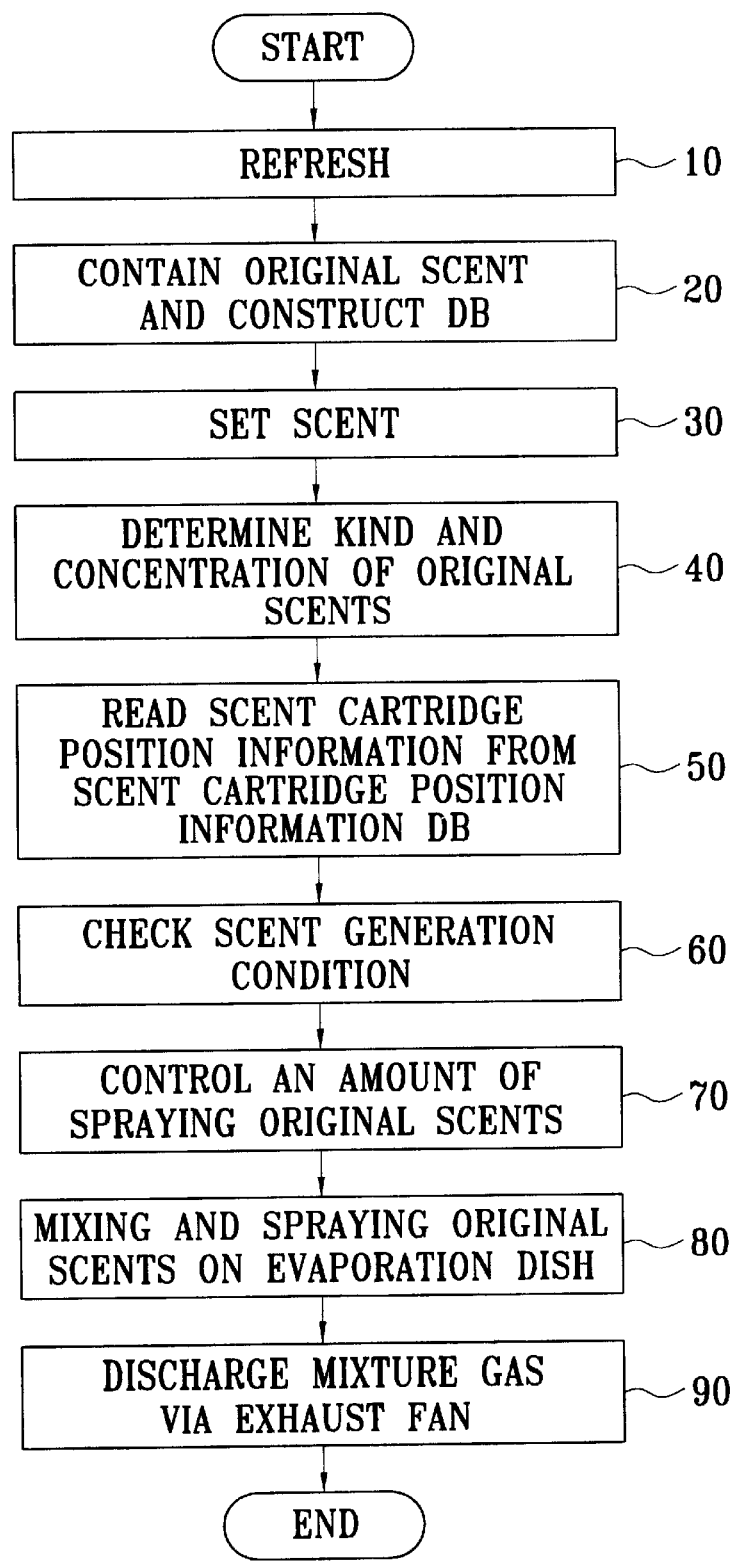
FIG. 10 is a flowchart for explaining the scent diffusion method of the FIG. 6 apparatus.

The operation of the scent diffusion apparatus as constructed above will be described with reference to a flowchart of FIG. 10. As an initial operation, the interior of the scent spraying unit 600 is refreshed (step 10). Then, original scents necessary for diffusing various scents are contained in a plurality of scent cartridges 650. It is preferable that each scent cartridge contains an original scent. If the original scents have been contained in the scent cartridges individually, position information of the scent cartridges 650 containing each of the respective original scents is constructed as a database and stored in a scent cartridge position information database 200. Also, the kind, constituent ratio, concentration and generation condition of the original scents to be mixed for generating various scents are constructed as a database and stored in the scent information database 300, with respect to each scent to be diffused (step 20).

If the database has been completely constructed and stored, the controller 100 sets a scent to be diffused (step 30). The controller 100 reads the kind, constituent ratio, concentration and generation condition of the original scents necessary for generating the set scent from the scent information database 300 (step 40). The generation condition includes a point in time when a scent is diffused, a scent diffusion duration time and a scent diffusion intensity. The controller 100 reads position information of the scent cartridges containing original scents necessary for diffusing a desired scent from the scent cartridge position information database 200 according to the scent information read from the scent information database 300 (step 50).

The controller 100 checks a generation condition from the read information and sets a diffusion point in time and a diffusion duration time in the timer 400 (step 60). If it reaches the diffusion point in time set in step 60, the controller 100 controls the scent spraying unit 600 via the control module 500 so that the original scents are sprayed from a corresponding scent cartridges 650, according to the information read from the databases 200 and 300 (step 70).

The controller 100 controls the selected scent cartridges individually, so that the original scents to be mixed are sprayed on the evaporation dish 630 accurately as much as the constituent ratio. If all the original scents to be mixed have been contained in the evaporation dish 630, the controller 100 supplies a control signal C3 for heating the original scents to a heater (not shown) of the evaporation dish 630 via the control module 500.

The original scents contained in the evaporation dish 630 are heated by the heater and evaporated (step 80). As a result, the evaporated gas includes all the corresponding original scents. It is preferable that at least a space necessary for maintaining the evaporated scent at a constant volume is provided in the scent spraying unit 600. The controller 100 supplies a control signal C4 to the exhaust fan 610 via the control module 500, to drive the exhaust fan 610. If the exhaust fan 610 has been driven, a mixture gas of the scent evaporated from the evaporation dish 630 and the air brought in via the intake hole 670 is discharged out of the sealing container 605 via the outlet hole 670' (step 90). The controller 100 can repeat the above operation so that a desired scent is generated repetitively. The controller 100 controls the electrically-driven intake opening and closing unit 620 to be driven so as to adjust an amount of air brought in via the intake hole 670. Likewise, the controller 100 controls the electrically-driven outlet opening and closing unit 620' to be driven so as to adjust an amount of the mixture gas discharged out via the outlet hole 670'.

Control signals C1 and C5 are generated in the control module 500 in order to control an amount of the opening and closing of the electrically-driven intake opening and closing unit 620 and the electrically-driven outlet opening and closing unit 620', respectively.

In the above-described embodiment of the present invention, it is preferable that the control module 500 for supplying control signals to the scent spraying unit 600 can be interfaced with a personal computer (PC) (not shown) as is well known in the art . It is also preferable that commands of the control module 500 can be compatible with control commands of a general purpose inkjet printer. By doing so, the control commands of a general purpose ink-jet printer which can be uses in connection with a standard interface with a personal computer can be compatibly used in the controller 100 in the scent diffusion apparatus according to the present invention. It is desirable in a point that an existing interface device can be directly applied. If commands compatible with those of a general purpose ink-jet printer are used, a mixture ratio of each liquid scent necessary for producing a desired scent can be set using a color mixture ratio of the general purpose ink-jet printer.

The scent diffusion apparatus according to the present invention can supplement each original scent in each scent cartridge individually, since each original scent is contained in its own scent cartridge 650.

The scent diffusion apparatus according to the present invention can be manufactured in a compact fashion, and control an amount of diffusion precisely since a spraying nozzle of a piezoelectric plate or thermal jet method which has been already testified in the ink-jet printer. Further, since the control commands which are used in the existing ink-jet printer can be compatibly used, the scent diffusion apparatus according to the present invention can be connected to a general purpose computer having all kinds of operating systems supporting the ink-jet printer.

Meanwhile, the scent diffusion apparatus according to the present invention provides the desired result of transferring a desired scent to a selected subject at a correct concentration, in which information on the kind, concentration and generating condition of the original scents to be combined is stored in a database in advance in order to produce a scent to be diffused, the original scents are evaporated as much as a predetermined amount based on the information, the evaporated scents are mixed with air, and then the mixed gas is pressed out to a selected subject according to a pressure difference.

The present invention can be modified in various forms. The present invention is not limited in the above-described embodiment. It is apparent to a person skilled in the art that there are many variations and modifications within the spirit and scope defined in the appended claims.

As described above, the scent diffusion apparatus according to the present invention does not spray a single scent but analyzes and itemizes components of various scents in a laboratory and mixes original scents to diffuse a desired particular scent in real-time based on the analyzed and itemized result. As a result, the present invention provides an apparatus and method which can represent scents in digital form. The present invention can be widely used in a scent treatment field, a remote medical operation field, a three-dimensional game and a simulation field, a virtual reality space experience, an education setting and so on. Also, the present invention can be applied to almost all kinds of products such as a mobile phone, a general telephone, a digital TV, a computer, a printer, a theater system, a building ventilation system, an aromatherapy medical device, a kiosk, a game machine, a clock, a presentation device, a ventilation system for an automobile, ship, airplane, and railway, a MP3 player, a CD player, a slot machine, an air-conditioner, a credit card device, and a refrigerator.

While only certain embodiments of the invention have been specifically described herein, it will be apparent that numerous modifications may be made thereto without departing from the spirit and scope of the invention.

What is claimed is:

1. A scent diffusion method, comprising the steps of;
   (a) storing a plurality of individual original scents;
   (b) constructing and storing a database containing information necessary for producing a scent to be diffused on a database, said database including the positions where each original scent is contained, and the kind, constituent ratio, concentration and diffusion condition of the original scents to be combined in order to make a set scent;
   (c) reading said information concerning said scent to be diffused from said database constructed in said step (b); and
   (d) mixing and spraying corresponding one or more individual original scents according to said information read in said step (c).

2. The scent diffusion method according to claim 1, wherein at least one of the individual original scents of said step (a) is contained in each of a plurality of scent spraying units.

3. The scent diffusion method according to claim 1, wherein the original scents of said step (a) are contained in a plurality of scent cartridges.

4. The scent diffusion method according to claim 3, wherein said diffusion condition comprises a diffusion point in time, a diffusion duration time and a diffusion intensity.

5. The scent diffusion method according to claim 2, wherein said diffusion condition comprises a diffusion point in time, a diffusion duration time and a diffusion intensity.

6. The scent diffusion method according to claim 5, wherein said step (d) comprises:
   (d1) driving a corresponding scent spraying unit and evaporating the original scents as much as a predetermined amount;
   (d2) uniformly mixing the scent evaporated in the corresponding scent spraying unit in said step (d1) with air, and producing a mixed gas to thereby produce a scent to be diffused; and
   (d3) pressing the scent made in step (d2) according to a pressure difference, to then be transferred to a selected subject.

7. The scent diffusion method according to claim 6, wherein the scent spraying unit is driven in said step (d1), so that a saturation rate of the evaporated original scent in each scent spraying unit is the same.

8. The scent diffusion method according to claim 7, wherein the evaporation rate depending upon a temperature of the original scent is differently set according to the position where each original scent is contained.

9. The scent diffusion method according to claim 6, wherein said step (d2) comprises the sub-steps of:
   (d2a) checking the diffusion condition, and supplying the air into the scent spraying unit containing the original scent to form the scent to be diffused, to thereby be mixed with the evaporated scent;
   (d2b) discharging the scent mixed with the air from each scent spraying unit; and
   (d2c) uniformly mixing the air mixture gases discharged from said each scent spraying unit.

10. The scent diffusion method according to claim 4, wherein said step (d) comprises the sub-steps of:
    (d1) individually spraying corresponding original scents as much as a predetermined amount;
    (d2) evaporating the corresponding original scents sprayed in said step (d1); and
    (d3) discharging a mixed gas of the evaporated scent and the air.

11. A scent diffusion apparatus comprising:
    a scent spraying unit including a plurality of individual original scents for diffusing and spraying a desired scent using at least one of said plurality of individual original scents from among the contained plurality of original scents;
    a first storing unit for storing position information of each of said individual original scents contained in said scent spraying unit;
    a second storing unit for storing information on said desired scent to be diffused, wherein said second storing unit constructs, in a database, the kind, constituent ratio, concentration and diffusion condition of at least one of said plurality of individual original scents necessary for diffusing said desired scent, and stores the same in said constructed database;
    a timer for setting a point in time of diffusion of said desired scent to be diffused; and
    a controller for reading individual scent position information regarding said plurality of individual original scents and said information on said desired scent to be diffused from said first storing unit and said second storing unit, for setting a scent diffusion point in time in said timer according to said information read from said first storing unit and said second storing unit, and for controlling said desired scent to be diffused in said scent spraying unit at said set scent diffusion point in time.

12. A scent diffusion apparatus comprising:
a scent spraying means including a plurality of individual original scents for diffusing and spraying a desired scent, said scent spraying means comprising a plurality of scent spraying units, wherein each of said scent spraying unit comprises:
a dispensing means for dispensing at least one of said plurality of scents;
a heater for evaporating said original scent in said container;
an intake unit for providing a source of intake air; and
an outlet unit for discharging a mixture containing said intake air mixed with said original scent evaporated by said heater;
a first storing unit for storing position information on each of said individual original scents contained in said scent spraying means;
a second storing unit for storing information on said desired scent to be diffused;
a timer for setting a point in time to diffuse said desired scent; and
a controller for reading individual scent position information regarding said plurality of individual original scents and said information on said desired scent to be diffused from said first store unit and said second store unit, for setting a scent diffusion point in time in said timer according to said information read from said first storing unit and said second storing unit, and for controlling said desired scent to be diffused in said scent spraying means at said set scent diffusion point in time.

13. The scent diffusion apparatus according to claim 12, wherein said second storing unit constructs, in a database, the kind, constituent ratio, concentration and diffusion condition of at least one of said plurality of individual original scents necessary for diffusing said desired scent, and stores the same in said constructed database.

14. The scent diffusion apparatus according to claim 13, wherein said diffusion condition comprises a diffusion point in time, a diffusion duration time and a diffusion intensity.

15. The scent diffusion apparatus according to claim 12, wherein said scent spraying means comprises:
an air supply pump, for supplying the air to said plurality of the scent spraying units;
a distributor, for distributing the air supplied from the air supply pump to said plurality of the scent spraying units;
a mixer, for uniformly mixing the scent diffused from the plurality of the scent spraying units with the intake air, to thereby produce a mixed gas; and
a scent provider, for transferring the uniformly mixed gas supplied from the mixer to a subject.

16. The scent diffusion apparatus according to claim 15, further comprising a dust collection and dehumidifying filter, for removing dust and humidity from the intake air supplied from said air supplying pump and said distributor.

17. The scent diffusion apparatus according to claim 15, further comprising a detour air path valve, for supplying air in which no scent is mixed between said distributor and said mixer, in order to adjust a concentration of the desired scent and to purge a residual scent.

18. The scent diffusion apparatus according to claim 12, wherein said first storing unit stores positions of said scent spraying units with respect to the original scents.

19. The scent diffusion apparatus according to claim 12, wherein said scent spraying unit further comprises an air intake solenoid valve, for controlling an amount of the air intake via said intake unit; and
an outlet solenoid valve, for controlling an amount of the air discharged via said outlet unit and the evaporated scent.

20. The scent diffusion apparatus according to claim 12, wherein said scent spraying unit comprises a space for maintaining said mixed gas in a constant volume.

21. The scent diffusion apparatus according to claim 15, wherein said scent provider is a tube for carrying the desired scent to reach the subject and wherein the desired scent supplied in front of the subject's nose.

22. The scent diffusion apparatus according to claim 21 wherein the scent is carried to the subject via compressed air.

23. A scent diffusion apparatus comprising:
a scent spraying means for diffusing and spraying a desired scent having a plurality of individual original scents, wherein said scent spraying means includes a single scent spraying unit comprising:
a plurality of scent cartridges storing said plurality of individual original scents individually;
spraying nozzles provided in each of said plurality of the scent cartridges for spraying said individual original scents contained in said scent cartridges;
an evaporation dish for evaporating at least one of said original scents after said original scent is sprayed from said scent cartridges via said spraying nozzles;
an air intake unit providing a source of intake air; and
an air outlet unit for discharging a mixed gas containing said original scents evaporated by said evaporation dish and said intake air;
a first storing unit for storing position information on each of said individual original scents contained in said scent spraying means;
a second storing unit for storing information on said scent to be diffused;
a timer for setting a point in time to diffuse said desired scent; and
a controller for reading individual scent position information regarding said plurality of individual original scents and said information on said desired scent to be diffused from said first store unit and said second store unit, for setting a scent diffusion point in time in said timer according to said information read from said first storing unit and said second storing unit, and for controlling said desired scent to be diffused in said scent spraying means at said set scent diffusion point in time.

24. The scent diffusion apparatus according to claim 23, wherein said first storing unit stores positions of said scent cartridges in said scent spraying units with respect to the original scents.

25. The scent diffusion apparatus according to claim 23, wherein said spraying nozzles are actuated in a piezoelectric plate method.

26. The scent diffusion apparatus according to claim 25, wherein said spraying nozzles intake a residual original scent when a spraying operation is terminated, and are closed with a cover at other times when the spraying operation is not being performed.

27. The scent diffusion apparatus according to claim 23, wherein said spraying nozzles are actuated in a thermal jet method.

28. The scent diffusion apparatus according to claim 27, wherein each of said spraying nozzles further comprises a heater, by which air bubbles in the spraying nozzles are heated and expanded, with a result that the original scent is sprayed and an amount of the sprayed original scent corresponds to the expanded volume of the air bubbles.

29. The scent diffusion apparatus according to claim 23, wherein said scent spraying unit further comprises an exhaust fan for discharging the mixed gas via said outlet unit.

30. The scent diffusion apparatus according to claim 29, wherein said scent spraying unit further comprises:
   a first opening and closing unit for controlling an amount air intake via said intake unit; and
   a second opening and closing unit for controlling an amount of the air discharged via said outlet unit and the evaporated scent.

31. The scent diffusion apparatus according to claim 30, wherein said first and second opening and closing unit are an electrically-driven opening and closing unit, respectively.

32. The scent diffusion apparatus according to claim 23, wherein said scent spraying unit comprises a space for maintaining said mixed gas in constant volume.

33. The scent diffusion apparatus according to claim 23, wherein said controller can be interfaced with a general-purpose computer.

34. The scent diffusion apparatus according to claim 23, wherein said controller can compatibly use control commands of a genreal-purpose ink-jet printer.

* * * * *